United States Patent [19]

Vlasov et al.

[11] Patent Number: 5,344,547
[45] Date of Patent: Sep. 6, 1994

[54] POLYCRYSTALLINE ION SELECTIVE ELECTRODE

[76] Inventors: Yuri G. Vlasov; Yuri E. Ermolenko, both of Chemistry Department, St. Petersburg University, St. Petersburg, 199034,

[21] Appl. No.: 999,287
[22] Filed: Feb. 18, 1993
[51] Int. Cl.$^5$ .............................. G01N 27/21
[52] U.S. Cl. .................. 204/419; 204/422; 204/416; 204/435
[58] Field of Search .............. 204/419, 418, 422, 416, 204/435

[56] References Cited

U.S. PATENT DOCUMENTS

| | | | |
|---|---|---|---|
| 3,591,464 | 7/1971 | Frant | 204/419 |
| 4,116,796 | 9/1978 | Havas et al. | 204/419 |
| 4,686,012 | 8/1987 | Engell et al. | 204/419 |
| 5,120,422 | 6/1992 | Liu et al. | 204/419 |

OTHER PUBLICATIONS

Yu. G. Vlasov, Yu. E Ermolenko, and O. A. Ishakova "Lead Containing Electrodes on the Basis of Lead and Silver Sulfides" UDC 543.257.1:546.815, at pp. 1522–1526, 1978. (Rough Draft translation provided). No month presently available.

J. Tacussel and J. J. Fomborn, "New Solid State Ion-Selective Electrodes for PO$_4{}^{3-}$ and Cl$^-$ Activity Measurements", Conference on Ion-Selective Electrodes—Budapest, 1977, at 567–562. No month presently available.

Y. G. Vlasov, "New Solid-State Ion-Selective Electrodes—Sensors for Chemical Analysis of Solutions" Fresenius Z Anal Chem (1989) 335:92–99.

J. Siemroth, I Henning and R. Claus, "All-SolidIon-Selective Electrodes Prepared from Fused Sensing Materials", 2nd Symposium on Ion-Selective Electrodes—MatraFured, 1976, at 185–189.

Yr. G. Vlasov and S. B. Kocheregin, "Structure and Electrical Properties of the Membranes of the Ion-Selective Electrodes Based on AgX—Ag$_2$S/X =Cl, Br, I/", Conference on Ion-Selective Electrodes—Budapest, 1977, at 597–601.

*Primary Examiner*—John Niebling
*Assistant Examiner*—Bruce F. Bell
*Attorney, Agent, or Firm*—Kokjer, Kircher, Bowman & Johnson

[57] ABSTRACT

An improved "all solid state" ion selective electrode device comprising a unique sensing element of triple-layer membrane construction. The first sensor layer of the sensing membrane comprising a solid electrolyte composition, the middle layer comprising a mixture of the aforesaid electrolyte composition and finely divided electronic conducting material, and the third contacting layer composed principally of the aforesaid electronic conducting material. The middle layer having a gradient of component concentration such that a substantial amount of the electrolyte composition is presented in the middle layer closest the first sensor layer and a substantial amount of the electronic conducting material is presented in the middle layer closest the third contacting layer.

25 Claims, 1 Drawing Sheet

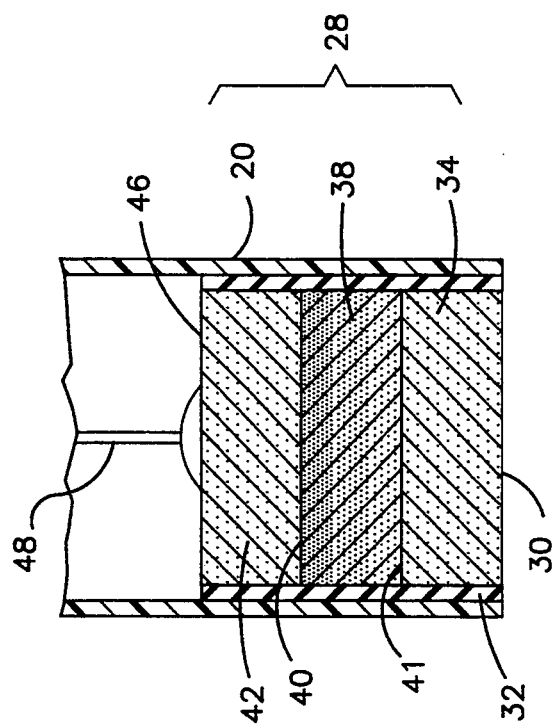
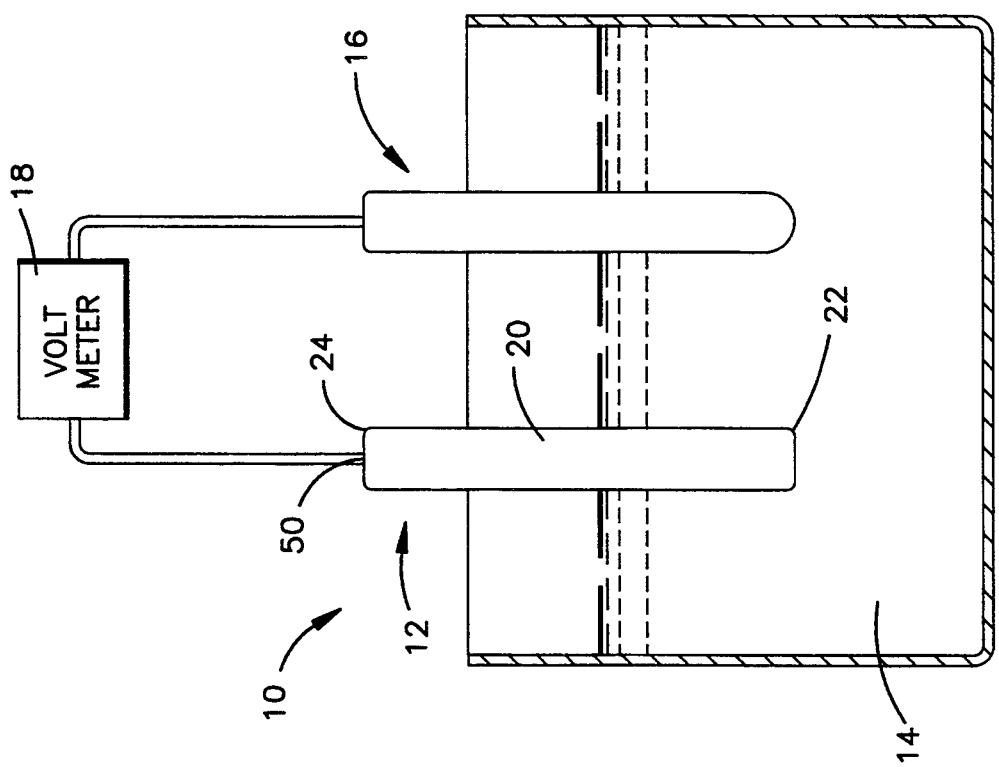

POLYCRYSTALLINE ION SELECTIVE ELECTRODE

BACKGROUND OF THE INVENTION

1. Field of the Invention

The present invention relates in general to electrochemical detection, and is more particularly directed to an "all solid state" ion selective electrode having a unique sensing element of triple layer construction. Other related embodiments of the invention include new solid electrolyte compositions for the selective determination of mercury and thallium ions whereby these compositions may be utilized in conjunction with the "all solid state" electrode disclosed herein.

2. Description of the Related Art

Ion selective electrodes (ISEs) have found wide practical application in the field of electrochemistry. Capable of detecting and measuring the concentration of a particular ionic species in solution, ISEs provide a useful analytical technique for the single measurement or continuous monitoring of flowing samples in solution. The applications of ISEs are numerous including biomedical research, clinical testing, industrial pollution testing and chemical-process control.

Solid state ISEs have been developed in the art which generally comprise a solid membrane as the sensing element which possesses ionic conductivity and is highly selective to a specific ionic species. In operation, one surface of the membrane is immersed in a sample solution of ions for which it is selective whereby a potential develops across the membrane surface at the interface of the solution and the membrane. This potential varies with the concentration of ions in solution and its magnitude is measured as a voltage. By comparing the voltage generated at the sensing membrane surface with that of a standard electrode of unvarying potential, it is possible to calculate the unknown solution's ion concentration.

A number of solid state membrane electrodes are patterned after glass electrodes consisting of the selective membrane affixed to the lower opening of a plastic barrel and having an inner electrolyte filler solution and reversible internal reference electrode sealed within. One problem encountered with ion-selective electrodes constructed of an internal reference electrode and internal solution is that weaknesses in the membrane seals can provide low resistance short-circuit pathways for ionic flow resulting in inaccurate measurements of membrane potential, particularly where constructed as a relatively small microelectrode such as that used in biomedical testing. In addition, those electrodes having an internal reference electrode and solution are relatively delicate instruments not particularly well suited for industrial or other practical field uses.

In order to overcome these problems, "all solid state" membrane electrodes have been developed which eliminate the inner filler solution and reference electrode and instead include a direct electrical contact to the inner surface (the surface not in contact with the sample solution) of the selective membrane. The membranes of these electrodes commonly include a polycrystalline pressed pellet of solid electrolytes and have a silver or gold plating on the membrane inner surface for electrical contact to a volt meter.

A variety of electrolyte compositions for use in "all solid state" membranes are known in the art that are selective to a specific ion. For example a pressed-pellet membrane comprising precipitates of silver sulfide is selective for $Ag^+$ or $S^{2-}$ ions. In addition, silver sulfides can be used in conjunction with silver halides or other sulfide salts to provide a whole series of heavy metal ISEs. [See e.g. U.S. Pat. No. 3,591,464 to Frant disclosing materials for the detection $Cl^-$, $Cu^{2+}$, $Br^-$, $I^-$, $SCN^-$, $Cd^{2+}$, and $Pb^{2+}$]. In order to expand the scope of already known and commercially available ion detectors, those in the art continue to seek new membrane compositions and materials that exhibit high selectivity toward a particular ionic species. To this end, in one embodiment of the present invention a novel membrane material is provided for the selective measurement of thallium ions. In another embodiment, a novel composition capable of detecting mercury is disclosed.

Although the "all solid state" electrode constructions heretofore developed in the art are relatively sturdy and particularly convenient for continuous industrial measurements and field use applications, it has proven difficult to provide the direct electrical contact as is required to the membrane surface at a fixed potential. This problem principally lies in the transition of charge transfer from ionic conductivity in the membrane to electronic conductivity in the electrical contact. Polarization distortion or blocking can occur at the junction between the metallic conductor and the sensing membrane which contributes or detracts from the potential at the membrane surface. This distortion affects an erroneous measurement of potential difference between the sample and standard reference resulting in inaccurate and inconsistent ion concentration measurements. To ease the transition of ionic conductivity and minimize this polarization effect, the present inventors heretofore developed a membrane construction of three layers: a first sensor layer comprising the electrolyte composition for contact with the sample solution, a middle layer comprising a uniform mixture of the electrolyte composition and silver powder, and a third layer of silver powder connected to a wire contact. [USSR Patent No. 630576 to Vlasov & Ermolenko]. The three layer system minimizes polarization effects to some extent, but the problem is not eliminated altogether, and meter drift and unreliability of measurement is still encountered.

It is therefore a primary object of the present invention to provide an improved all solid state ion selective electrode for detecting and measuring the presence of ions in solution.

It is another object of the present invention to provide an improved all solid state electrode having a relatively high level of stability of potential across the sensing membrane.

Another object of the present invention is to provide an all solid state ion selective electrode that is durable and that exhibits effectiveness for extended in use service.

A further object of the present invention is to provide an all solid state ion selective electrode that exhibits high precision and reliability of measurement.

It is also an object of the present invention to provide an all solid state ISE which permits on-stream monitoring of ion activity.

Yet another object of the present invention is to provide an all solid state ISE having a sensing membrane constructed to achieve all the objects heretofore set forth.

A further object of the present invention is to provide a novel electrolyte composition that is highly selective to mercury.

It is yet a further object of the present invention to provide a novel electrolyte composition selective for thallium.

These and other objects are achieved by an improved "all solid state" ion selective electrode having a unique sensing element comprising a polycrystalline membrane of triple-layer construction. The first sensor layer of the membrane is composed of a solid electrolyte composition selective to a specific ion in solution, the intermediate or middle layer is comprised of a mixture of the aforesaid electrolyte composition of the sensor layer and a finely divided electronic conducting material, and the third electrical contacting layer is composed principally of the aforementioned material having electronic conductivity. The improvement being that the intermediate (middle) layer has a gradient of component concentration such that a substantial amount of the electrolyte composition is presented in the middle layer closest the sensor layer and a substantial amount of the electronic conducting material is presented in the middle layer closest the electrical contacting layer. The layers are pressed together under pressure and in the presence of heat to provide a substantially non-porous polycrystalline ceramic membrane. This unique construction provides an electrode that has an extremely high level of stability of potential across the surface of the membrane and which exhibits excellent precision and reliability of measurement during long term operation.

Although the inventors do not wish to be limited by theory, it is hypothesized that the gradient of concentration in the intermediate layer enables relatively continuous and "easy" passage from pure ionic conductivity at the surface of the sensor layer, where the potential has been created, to pure electronic conductivity at the electrical contacting layer.

In a related embodiment of the invention, a novel solid electrolyte composition is provided for the determination of mercury, wherein the composition comprises a mixture of thallium iodide (TlI) and silver iodide (AgI). A novel electrolyte composition comprising $Ag_8HgS_2I_6$ and a method of preparing the same is also provided, wherein the composition is useful for the measurement of mercury. These new electrolyte compositions may be used in conjunction with the sensing element of the present invention or with any conventional ISE now known or later developed in the art.

DESCRIPTION OF THE DRAWINGS

FIG. 1 shows an ion sensitive measuring assembly embodying the principles of the present invention. The assembly includes an "all solid state" ion selective electrode device made in accordance with the present invention wherein the device and an external reference connected to a readout device are immersed in an unknown sample solution for testing. The ion concentration of the sample solution is determined by measuring the potential difference over the selective device and that of the external reference.

FIG. 2 is a cross-sectional view of the electrode device of FIG. 1 having a unique triple-layer membrane as the sensing element.

DETAILED DESCRIPTION OF THE DRAWINGS AND THE INVENTION

Referring to FIG. 1, an ion sensitive measuring assembly according to the present invention is generally designated by the numeral 10. The assembly 10 comprises an "all solid state" ion selective electrode device 12 immersed into a sample solution 14 of unknown ion concentration. A standard external reference electrode 16 is also placed in contact with solution 14. Both the selective electrode 12 and reference electrode 16 are connected electrically to respective inputs of a readout meter 18 such as a potentiometer or voltmeter to display the voltage or potential difference over the selective electrode 12 and the external reference 16 in millivolts (mV) or concentration units.

The selective electrode device 12 comprises an elongated hollow cylindrical housing 20 of electrically insulating material preferably formed of a liquid impervious, rigid, highly resistant material, that is substantially chemically inert to the solution 14 being tested. Suitable materials include polyethylene, polystyrene, unplasticized polyvinyl chloride and polytetra-fluorethylene. The cylindrical housing 20 having an open bottom 22 to be immersed in the test solution and a closed top 24.

Looking to FIG. 2, the sensing membrane 28 is of triple layer sheet-like construction providing a pair of exposed faces between which ionic and electronic charge transfer is effected. The membrane is of a diameter to fit snugly within the confines of the housing 20, wherein the lower exposed face 30 of membrane element 28 is positioned within the hollow cylinder such that the peripheral surface of lower face 30 is adjacent the lower edge of open bottom 22. In this manner, a substantial portion of the lower exposed face 30 is in direct contact with the sample solution 14. It is important that the membrane 28 be sealed within the cylinder such that fluid leakage along lower membrane face 30 is prevented. An epoxy resin 32 or similar sealing material may be provided along the interior circumference of the cylindrical housing in continuous contact with the outer edges of the membrane.

The sensing element 28 is a solid non-porous, preferably ceramic, membrane of compressed polycrystalline material and includes three layers of differing composition. The sensor layer 34 is relatively flat having a lower exposed face 30 as heretofore mentioned for contact with the sample solution and an inner surface 36 adjacent to and in immediate contact with the second middle layer 38. The relatively flat middle layer 38 having upper and lower surfaces 40 & 41 respectively is sandwiched between and in contact with sensor layer 34 and the third contacting layer 42. Contacting layer 42 is relatively flat having a lower surface adjacent to and in immediate contact with the upper surface 40 of the middle layer 38, and an upper exposed face 46 in contact with an electrical contact wire 48. The wire 48 may comprise any electronic conductive material such as a silver, gold or copper wire and is placed in contact with upper exposed face 46 by soldering to the face, by use of an epoxy resin or by use of a conducting sealing compound. Wire 48 extends through an aperture 50 in the closed top 24 of housing 20 for connection to the readout meter 18.

The meter 18 may be a high impedance ($10^9$ ohm) volt meter (mV-meter), or, in view of the low resistivities of the electrode of the present invention (1–10 kohm), measurements may also be performed with relatively low impedance measuring instruments. The choice of reference electrode may depend upon the specific ion being tested and may include a conventional calomel electrode (S.C.E.) having a salt bridge, or a double junction electrode having an electrolyte bridge such as that filled with a nitrate solution.

In operation, a potential $E_0$ of substantially fixed value, known as the standard potential, develops between the external reference electrode 16 and the sample solution 14 independently of the ion concentration of the solution. A second potential $E_m$, will develop on the surface of sensor membrane and varies logarithmically according to the activity or concentration of specific (determinate and/or certain) ions in solutions. The difference in these potentials is measured as E by the mV-meter and the concentration of the ionic species in sample solution can then be determined by reference to a standard calibration curve or may be directly read from a specific ion meter. Other suitable methods of determination can be utilized in conjunction with the electrodes of the present invention such as incremental addition or titration techniques.

The important features of the present invention lie in the construction of the triple-layer sensing membrane element 28. The other components of the ion sensitive assembly and the shape and size of the electrode device are not particularly critical and can be selected according to anticipated use and other practical considerations.

The first sensor layer 34 of membrane element 28 is comprised of a solid electrolyte composition which possesses ionic conductivity and is selective or particularly sensitive to a specific ion in solution. Any conventional electrolyte compositions now known or later developed in the art are suitable for purposes of the present invention, however it is important to note that a common electrically charged component need be present in all three layers of the selective membrane to achieve thermodynamic equilibrium during charge transfer. The crystalline electrolyte mixtures of the sensor layer may be obtained by various methods widely known in the art, including coprecipitation of salts from aqueous solutions, by precipitating the mixture from solutions of thiourea or by fusing the crystalline components.

In a preferred embodiment of the invention, the common charged component of the three layers is silver wherein the electrolyte selective composition includes an amount of silver as in the form of $Ag_2S$ or $Ag_2I$ and the electronic conducting material of the electrical contacting layer as heretofore mentioned is comprised of finely divided silver. A number of "silver based" electrolyte compositions are provided by intimately and uniformly mixing $Ag_2S$ with another compound selected according to the desired response of the electrode.

Where it is desired to determine the presence of silver and/or sulphur ions, a composition of 100% $Ag_2S$ is utilized. [U.S. Pat. No. 3,672,962 to Frant which discloses detecting sulfide ion with a composition of high purity silver sulfide substantially free of metallic silver]. If the electrode is to be sensitive to copper ($Cu^{++}$) ions, the composition may comprise copper sulfide and silver sulfide, the mole percentage amount of each component ranging from 30% $CuS$:70% $Ag_2S$ to 70% $CuS$:30% $Ag_2S$. A composition useful for the detection of lead ions ($Pb^{++}$) may include a mixture of lead sulfide and silver sulfide wherein the amount of each in mole percentage amounts preferably ranges from 30% $PbS$:70% $Ag_2S$ to 70% $PbS$:30% $Ag_2S$. Cadmium ions ($Cd^{++}$) may be detected utilizing a mixture of cadmium sulfide and silver sulfide in amounts ranging from 30% $CdS$:70% $Ag_2S$ to 70% $CdS$:30% $Ag_2S$ (mole percentage). A composition selective for the presence of chlorine ions ($Cl^-$) includes a mixture of silver chloride and silver sulfide where the preferred mole percentage ratios range from 30% $AgCl$:70% $Ag_2S$ to 70% $AgCl$:30% $Ag_2S$. Bromine ions ($Br^-$) can be measured with a composition comprising silver bromide and silver sulfide wherein the amount of each component in mole percent amounts ranges from 30% $AgBr$:70% $Ag_2S$ to 70% $AgBr$:30% $Ag_2S$.

An electrode device selective for iodine ($I^-$) and cyanide ($CN^-$) ions may comprise an electrolyte composition of silver iodide and silver sulfide in mole percentage ratios ranging from 30% $AgI$:70% $Ag_2S$ to 70% $AgI$:30% $Ag_2S$. A suitable composition selective for thiocyanate ($CNS^-$) includes a mixture of silver thiocyanate and silver sulfide wherein the amount of each component ranges in mole percent from 30% $AgCNS$:70% $Ag_2S$ to 70% $AgCNS$:30% $Ag_2S$.

For the detection of thallium ($Tl^+$), the present inventors have developed a new selective composition which comprises a mixture of thallium iodide (TlI) and silver iodide (AgI). The thallium iodide is provided in the mixture in an amount ranging from 30 to 50% mole percent with the remainder being silver iodide. In a preferred embodiment, the composition of the thallium selective material comprises 30% TlI and 70% AgI in mole percentage amounts. It has been discovered that this composition is particularly suited for the determination of thallium ions exhibiting high selectivity and reproducibility of results.

In another embodiment, a selective composition that may be utilized for the measurement of mercury ions ($Hg^{++}$) is comprised of the new compound $Ag_8Hg$-$S_2I_6$. This compound may be formed by the solid phase reaction of AgI, $Ag_2S$ and $HgI_2$ with heating.

The sensing membrane element 28 may of course be based upon other commonly charged particles in each layer. For example, it is known in the art to provide a selective composition sensitive to halide ($X^-$) ions comprising a mixture of a solid amalgam or gold and mercury with a finely divided mercurous halide salt. [U.S. Pat. No. 4,211,623 to Amass et al.]. A sensor element may thus be provided utilizing this mercurous halide composition as the electrolyte composition and finely divided gold or mercury as the electronic conducting material.

The middle layer 38 of the sensing membrane element 28 comprises a mixture of the solid electrolyte composition of the first sensor layer as heretofore described in an amount ranging from 30 to 70% by total weight and the electronic conducting material of the third layer presented in an amount ranging from 30 to 70% by weight of the total middle layer. For best results, it is suggested that the electrolyte composition and the electronic conducting material be provided in equal amounts of 50% electrolyte and 50% conducting material.

An important feature of the present invention lies in the unique gradient of component concentration provided in the middle layer, whereby a substantial amount of the electrolyte composition is present in middle layer 38 nearest the first sensor layer 34 and the electronic conducting material is present in substantial amount nearest the third contacting layer 42. Preferably, the gradient of concentration is "uniform", meaning the lower surface 41 of the middle layer in contact with the sensor layer 34 is substantially uniformly comprised of the electrolyte composition, and the concentration of the electrolyte composition in the middle layer gradually decreases toward its upper surface 40, (that surface which is in contact with the third contacting layer). Furthermore, the upper surface 40 of the middle layer is substantially uniformly comprised of the electronic conducting material and the concentration of such material in the middle layer gradually decreases toward its lower surface 41, (that surface which is in contact with the sensor layer).

The middle layer having a gradient of component concentration may be formed through the use of sieves or any other means now known or later developed in the art. In a preferred embodiment, the layer is formed by passing a uniform mixture of the electrolyte composition and the conducting material through a series of stacked sieves having varied sizes. As the electrolyte composition particles are generally heavier or lighter in weight or larger or smaller in particle size than that of the finely divided conducting material, the sieves can be arranged such that passage of these particles through the sieves provides a layer of "uniform" gradient as heretofore described.

The third contacting layer 42 of sensing membrane 28 comprises an electronic conducting material, preferably a material containing a commonly charged particle with that of the sensor layer as heretofore described. Suitable materials include gold or silver that is finely divided, preferably in near powder form and most preferably of a particle size ranging from 20 to 50 micrometers.

The multi-layer sensing membrane element is prepared by stacking the components of the three layers; the sensor layer, the middle layer and the contacting layer, one above the other in a cylindrical die or pellet press and compressing the layers with heat to form a substantially non-porous polycrystalline ceramic membrane. After pressing, each layer of the membrane should be of relatively uniform thickness ranging from about 0.8 to 1.2 millimeters (mm). The diameter of the membrane will, of course, depend upon the electrode housing but will generally range from about 6 to 10 mm. The membrane faces are finished by polishing prior to placement in the electrode housing.

The following examples of the preparation of sensor membranes made in accordance with the invention and the responses of all solid state selective electrodes using such membranes are for purposes of illustration only.

EXAMPLE I

Preparation of Electrolyte Composition for the Detection of Lead

An electrode for the selective detection of lead ions ($Pb^{++}$) was prepared in accordance with the present invention, wherein the solid electrolyte composition of the sensor layer comprised a mixture of PbS and $Ag_2S$. The electrolyte composition was prepared by mixing a solution of 0.1M $AgNO_3$ and 0.1M $Pb(NO_3)_2$ and then adding said mixture drop by drop to an excess amount (1-2% opposite stoichiometry) of an $Na_2S$ solution. This order of mixing avoids the primary precipitation of $Ag_2S$ in comparison with PbS.

After the precipitate settled, the slurry was decanted with subsequent washing with water until a negative reaction to sulfide-ion ($S^{2-}$) was obtained. The precipitate was then dried at about 70°-80° C. The final mixed powder is utilized in preparing the sensor layer and the middle gradient layer of the electrode device.

EXAMPLE II

Preparation of Electrolyte Composition for the Detection of Cadmium

An electrolyte composition for the detection of cadmium $Cd^{++}$ comprising a mixture of CdS and $Ag_2S$ was prepared according to Example I excepting that the salt $Cd(NO_3)_2$ was used in place of $Pb(NO_3)_2$.

EXAMPLE III

Preparation of Electrolyte Composition for the Detection of Copper

An electrolyte composition for the detection of copper $Cu^{++}$ comprising a mixture of CuS and $Ag_2S$ was prepared according to Example I excepting that the salt $Cu(NO_3)_2$ was used in place of $Pb(NO_3)_2$.

EXAMPLE IV

Preparation of Electrolyte Composition for Detection of Thiocyanate

An electrolyte composition for the detection of thiocyanate $CSN^-$ comprising a mixture of AgCNS and $Ag_2S$ was prepared according to Example I excepting that aqueous solutions of 0.1M KCSN and 0.1M $Na_2S$ were mixed together and then the mixture was added drop by drop to a solution of excess $AgNo_3$ (1-2%) to effect precipitation.

EXAMPLE V

Preparation of Electrolyte Composition for Chloride Detection

An electrolyte composition for the detection of chloride ions ($Cl^-$) comprising AgCl and $Ag_2S$ was prepared. The precipitation was carried out from aqueous solutions by adding a solution mixture comprising 0.1M NaCl and 0.1M $Na_2S$ (by drops) to an excess of $AgNo_3$ (1-2%) solution. The precipitates were washed and dried under vacuum at room temperature.

EXAMPLE VI

Preparation of Electrolyte Composition for Bromide Detection

An electrolyte composition for the detection of bromide $Br^-$ comprising a mixture of AgBr and $Ag_2S$ was prepared as in Example V above excepting that KBr is used in place of NaCl.

EXAMPLE VII

Preparation of Electrolyte Composition by Furnacing (Baking)

An electrolyte composition for the detection of lead ions may also be obtained by furnacing and/or baking the powders of lead, silver and sulfur in appropriate ratios. The furnacing may be carried out in a quartz ampoule evacuated to about 13 Pascals (Pa) or in systems filled with hydrogen sulfide, and by heating to about 400° C. for 6 hours. After slow cooling, the final product is prepared by grinding the mixture of sulfides to a grain size ranging from 20 to 50 micrometers.

EXAMPLE VIII

Preparation of Electrolyte Composition Selective to Mercury

A mercury electrolyte composition in accordance with the present invention comprising $Ag_8HgS_2I_6$ was obtained by means of a two-stage solid-phase reaction. The starting materials for this reaction comprised a mixture of $AgI:Ag_2S:HgI_2$ in the mole percentage amounts of 57,1:28,6:14,3. The reaction mixture was compressed (2000 kg/cm$^2$) and first heated to a temperature of 400° C. with constant heating for three(3) hours in a dry inert atmosphere. The reaction product was then ground, compressed, and heated to the temperature 400° C. for 3 hours in the same dry inert atmosphere. X-ray diffraction analysis showed the formation of $Ag_8HgS_2I_6$ with body-centered cubic structure.

EXAMPLE IX

Preparation of Electrode Composition Selective to Thallium

A solid electrolyte composition for the detection of thallium ions comprising TlI and AgI was prepared. The preparation was carried out from aqueous solutions by adding a mixture comprising 0.03M $TlNO_3$ and 0.07M $AgNO_3$ (by drops) to an excess of 0.1M NaI solution (1-2% excess in comparison with stoichiometry composition).

EXAMPLE X

Preparation of the Middle Layer with Uniform Gradient

An electrolyte composition of the first sensor layer as described above is placed in a die or pellet press and the middle layer is placed on top of the sensor layer by placing four (4) sieves 0.5 to 1.0 centimeters apart one above the other in the die each having a pore size of 60—60-40—40 μm (micrometers) respectively (from the bottom up). Equal molar amounts of the electrolyte composition and electronic conducting material of finely divided silver (20 to 50 μm) are thoroughly mixed and placed on the top sieve. The die is shaken such that the mixture passes through the sieves by gravity to form a desired relatively "uniform" gradient of component composition in accordance with this invention. The choice of sieve pore sizes may vary depending upon the size and weight of the two compositions.

EXAMPLE XI

Preparation of Ceramic Membrane of Three-Layer Construction

A layer of finely divided silver powder (20 to 50 μm) is placed above the gradient middle layer in the die of Example X above. The layers were then compressed, typically at a pressure of 8000-9000 kg/cm$^2$, at a temperature of about 90°-110° C. for a period of about 2 minutes, and preferably under a moderate vacuum during compression. The exposed surfaces of the resulting ceramic membrane were then polished prior to inclusion in the electrode housing.

EXAMPLE XII

Preparation of Calibration Curve

A sensor membrane for the detection of thiocyanate ions CSN$^-$ in prepared in accordance with Examples IV, X and XI above. To obtain calibration, the response of the membrane to standard solutions of concentrations ranging from $10^{-5}$ to 0.1 mole thiocyanate ion per liter solution (mol/l) was plotted. A stock solution of 0.1 mol/l was prepared from reactive grade sodium thiocyanate by weight and other solutions were prepared by consequent tenfold dilution with 0.1 mol/l potassium nitrate.

The ion selective electrode is connected to a high impedance ($10^9$ Ohm) volt digital meter or ion analyzer. A double junction electrode with electrolyte bridge filled with 0.1 mol/l potassium nitrate solution was used as a reference electrode. The potassium nitrate filling solution of different concentrations may be required for certain test. The solutions were tested at a temperature of 25° C. as 20 ml samples.

The dependence of emf of the cell from $-1$ g $a_{CNS-}$ obeys the Nernst equation:

$$E = E^0 - S \, \lg a_{CNS-} \qquad \text{[Equation I]}$$

in the concentration range from $10^{-5}$ to 0.1 mol/l CNS$^-$. The values of $-1$ g $a_{CNS-}$ in the standard solutions are plotted to determine slope (S). Ten fold change in activity or concentration of standard solutions (for solutions with constant ionic strength) is equal to the change of unit in scale $-1$ g $a_{CNS-}$ or pCNS. This is analogous to Ph-scale wherein Ph $= -1$ g $a_{H+}$ in solution.

EXAMPLE XIII

Analytical Characteristics of the Electrodes of the Present Invention

The response of several selective electrodes made in accordance with the present invention to standard solutions is recorded below. The membranes responded substantially in accordance with the Nernst Equation (I) above in a stable and reproducible manner in the concentration sensitivity ranges listed. The electrical resistance of the electrodes was relatively low ranging from 1 to 5 kohm.

TABLE I

| Ion | Electolyte Composition | Sensitivity Range (Molar) | Temperature Interval (°C.) | Slope (mV/pX) | pH range |
|---|---|---|---|---|---|
| $^1$Cl$^-$ | AgCl—Ag$_2$S | $3 \times 10^{-5} - 1.0$ | 0–80 | 58–59 | 2–8 |
| $^2$Br$^-$ | AgBr—Ag$_2$S | $10^{-6} - 1.0$ | 0–80 | 58–59 | 1–12 |
| $^3$I$^-$ | AgI—Ag$_2$S | $5 \times 10^{-7} - 0.1$ | 0–80 | 58–59 | 1–12 |
| $^4$CN$^-$ | AgI—Ag$_2$S | $10^{-6} - 0.01$ | 0–80 | 56–58 | 11–13 |
| $^5$CNS$^-$ | AgCNS—Ag$_2$S | $10^{-5} - 0.1$ | 0–80 | 56–58 | 2–10 |
| $^6$S$^{2-}$ | Ag$_2$S | $10^{-7} - 0.1$ | 0–80 | 28–29 | 12–14 |
| $^7$Ag$^+$ | Ag$_2$S | $10^{-7} - 1.0$ | 0–80 | 58–59 | 1–12 |
| $^8$Cu$^{2+}$ | CuS—Ag$_2$S | $10^{-7} - 1.0$ | 0–80 | 28–29 | 1–7 |
| $^9$Pb$^{2+}$ | PbS—Ag$_2$S | $3 \cdot 10^{-7} - 0.1$ | 0–80 | 28–29 | 3–7 |
| $^{10}$Cd$^{2+}$ | CdS—Ag$_2$S | $3 \cdot 10^{-7} - 0.1$ | 0–80 | 27–29 | 1–8 |
| $^{11}$Tl$^+$ | TlI—AgI | $3 \cdot 10^{-5} - 0.1$ | 0–80 | 57–59 | 2–7 |

TABLE I-continued

| Ion | Electolyte Composition | Sensitivity Range (Molar) | Temperature Interval (°C.) | Slope (mV/pX) | pH range |
|---|---|---|---|---|---|
| [12]$Hg^{2+}$ | $Ag_8HgS_2I_6$ | $10^{-6} - 0.1$ | 0–80 | * | 1–2 |

* Slope depends on the concentration range.
[1] Interfering ions include $S^{-2}$, $CN^-$ and $CNS^-$. Selectivity in the presence of $Br^-$ is reduced to about $8 \times 10^2$ and in the presence of $I^-$ is $1 \times 10^4$.
[2] Interfering ions include $S^{-2}$, $CN^-$ and $CSN^-$. Selectivity in the presence of $Cl^-$ is about $3 \times 10^{-3}$ and in the presence of $I^-$ is about $1 \times 10^4$.
[3] Interfering ions include $S^{-2}$, $CN$ and $CSN^-$. The selectivity in the presence of $Cl^-$ is about $10^{-4}$ and in the presence of $Br^-$ is about $1 \times 10^{-3}$.
[4] A background solution of .01 mol/l of potassium hydroxide (pH = 12) was added to the samples to retain high pH of at least 11. $S^{-2}$ is an interfering ion. The selectivity coefficient in the presence of iodide is about unity.
[5] Interfering ions include sulfide ions and relatively high concentrations of $Cl^-$, $Br^-$ and $I^-$ can effect the determination.
[6] The sample solution was mixed with an equal amount of an freshly prepared antioxidizing buffer prepared from 80 g of sodium hydroxide diluted in 500 ml deoxygenated water. Ascorbic acid was added (72 g) and the total volume is adjusted to 1 liter. No anions interfere with sulfide determination significantly.
[7] Interfering ion is $Hg^{2+}$ only.
[8] Interfering ions include $Ag^+$ and $Hg^{2+}$.
[9] Interfering ions include $Ag^+$, $Hg^{2+}$, $Cu^{2+}$ and high concentrations of $Cd^2$.
[10] Interfering ions include $Ag^+$, $Hg^{2+}$, $Cu^{2+}$ and high concentrations of $Pb^2$.
[11] Interfering ions include $Ag^+$ and $Hg^{2+}$.
[12] Interfering ion is $Ag^+$ only.

EXAMPLE XIV

Measurement of Unknown Ion Concentration

In use, the measured E value obtained by measuring the potential difference between the selective electrode and reference electrode can be compared with a calibration plot or converted into pX to determine ion concentration in the sample. Analytical response time is usually not more than sixty (60) seconds. To improve reliability of results, the calibration plot should be tested daily during measurements and corrected if necessary. Before use of the ion-selective electrode in diluted solutions, it should be washed with distilled water to as low potential values as possible. The electrode used for measurements in diluted solutions is not recommended for the determination of ions in concentrated media. After measurements, the ion-selective electrodes should be washed by distilled water and stored dry. Ion determination in strongly acid media is also possible but only short-time measurements should be carried out because of partial membrane dissolution. Soft mechanical grinding may be useful in the case of response deterioration.

EXAMPLE XV

Reliability of Potential Measurement

The amount of meter drift in the measurement of E in millivolts (mV) over a five (5) minute interval was measured using a control electrode device and a device made in accordance with Example I for the detection of lead. The control electrode device comprises a ceramic membrane of triple layer construction and is prepared as described in Examples X and XI excepting that the components of the middle layer, namely a selective composition of lead sulfide/silver sulfide ($PbS/Ag_2S$) and silver powder are uniformly and intimately mixed throughout the middle layer as opposed to having a gradient of component composition.

TABLE II

| | Drift of E in solution $10^{-2} - 10_{-4}M$ (mole) | Change E in month |
|---|---|---|
| A. Control | .5 mV/10 min | 3–5 mV |
| B. Membrane w/gradient | .2 mV/10 min | 1 mv |

I claim:

1. A polycrystalline membrane for the detection of an ionic species in solution, said membrane comprising:
   a first sensor layer composed of a solid electrolyte composition possessing ionic conductivity;
   a second middle layer comprising a mixture of said solid electrolyte composition and an electronic conducting material, whereby said middle layer has a gradient of component concentration such that a greater amount of said electrolyte composition is presented in said middle layer closest said sensor layer than is presented near said third contacting layer, and a greater amount of said electronic conducting material is presented in said middle layer closest said third contacting layer than is presented near said first contacting layer; and
   a third electrical contacting layer comprising said electronic conducting material.

2. A membrane in accordance with claim 1 wherein said gradient of component concentration is uniform.

3. A membrane in accordance with claim 1, wherein said membrane comprises a ceramic membrane of compressed polycrystalline material.

4. A membrane in accordance with claim 1, wherein said sensor layer has a lower exposed face for contact with said solution.

5. A membrane in accordance with claim 4, wherein said middle layer has upper and lower surfaces and being sandwiched between and in contact with said sensor layer and said third contacting layer.

6. A membrane in accordance with claim 5, wherein said third contacting layer has an upper exposed face in contact with an electrical wire.

7. A membrane in accordance with claim 5, wherein said gradient of concentration is uniform, such that said lower surface of said middle layer is uniformly comprised of said electrolyte composition and the concentration of said electrolyte composition in said middle layer gradually decreases toward said upper surface of said middle layer, and wherein said upper surface of said middle layer is uniformly comprised of said electronic conducting material and the concentration of said material in said middle layer gradually decreases toward said lower surface of said middle layer.

8. A membrane in accordance with claim 1 wherein said electrolyte composition is selective toward a specific ion in said solution.

9. A membrane in accordance with claim 8 wherein said electrolyte composition includes a silver component.

10. A membrane in accordance with claim 9 wherein said silver component is selected from the group consisting of silver sulfide, silver iodide, silver bromide, silver chloride, silver iodide, silver cyanate, $Ag_8HgS_2I_6$ and mixtures thereof.

11. A membrane in accordance with claim 10 wherein said silver component is mixed with a sulfide salt.

12. A membrane in accordance with claim 11 wherein said sulfide salt is selected from the group consisting of copper sulfide, lead sulfide and cadmium sulfide.

13. A membrane in accordance with claim 10 wherein said silver component is mixed with thallium iodide.

14. A membrane in accordance with claim 13 wherein said electrolyte composition is selective for thallium, said composition comprising a mixture of thallium iodide (TlI) and silver iodide (AgI).

15. A membrane in accordance with claim 14 wherein said thallium iodide is provided in the mixture in a amount ranging from 30 to 50% mole percent with the remainder being silver iodide.

16. A membrane in accordance with claim 15 wherein said composition comprises 30% TlI and 70% AgI in mole percentage amounts.

17. A membrane in accordance with claim 9, wherein said electronic conducting material is metallic silver.

18. A membrane in accordance with claim 17, wherein said metallic silver is finely divided ranging from 20 to 50 micrometers in particle size.

19. An all solid state ion selective electrode device for the detection of a particular ion species in solution, said device comprising:
a polycrystalline membrane having a first sensor layer composed of a solid electrolyte composition possessing ionic conductivity, a second middle layer comprising a mixture of said solid electrolyte composition and an electronic conducting material, and a third electrical contacting layer comprising said electronic conducting material, wherein said middle layer has a gradient of component concentration such that a greater amount of said electrolyte composition is presented in said middle layer closest said sensor layer than is presented near said third contacting layer, and a greater amount of said electronic conducting material is presented in said middle layer closest said third contacting layer than is presented near said first contacting layer.

20. An electrode device in accordance with claim 19, wherein said sensor layer has an exposed lower face for contact with said solution.

21. An electrode device in accordance with claim 20, wherein said membrane is provided within a housing such that only the said lower face of said sensor layer comes into direct contact with said solution upon immersing said housing into said solution.

22. An electrode device in accordance with claim 19, wherein said third contacting layer has an upper exposed face in contact with an electrical wire.

23. An electrode device in accordance with claim 22, wherein said electrical wire is connected to a readout meter.

24. An electrode device in accordance with claim 23, wherein said readout meter is a volt meter.

25. An electrode device in accordance with claim 23, wherein said readout meter is also connected to an external reference electrode.

* * * * *